(12) United States Patent
Correa de Mendonca

(10) Patent No.: US 9,107,714 B2
(45) Date of Patent: Aug. 18, 2015

(54) MULTIFUNCTIONAL PLATE FOR NEUROLOGICAL CRANIAL SURGERIES

(71) Applicant: Roberto Correa de Mendonca, Sao Paulo (BR)

(72) Inventor: Roberto Correa de Mendonca, Sao Paulo (BR)

(*) Notice: Subject to any disclaimer, the term of this patent is extended or adjusted under 35 U.S.C. 154(b) by 85 days.

(21) Appl. No.: 13/713,098

(22) Filed: Dec. 13, 2012

(65) Prior Publication Data

US 2013/0172941 A1  Jul. 4, 2013

(30) Foreign Application Priority Data

Dec. 16, 2011 (BR) ...................................... 1105137

(51) Int. Cl.
   *A61B 17/80* (2006.01)
(52) U.S. Cl.
   CPC .................................. *A61B 17/8061* (2013.01)
(58) Field of Classification Search
   CPC .................................................... A61B 17/8061
   USPC ............................................ 606/70, 280–299
   See application file for complete search history.

(56) References Cited

U.S. PATENT DOCUMENTS

| | | | | |
|---|---|---|---|---|
| 5,578,036 A | * | 11/1996 | Stone et al. | 606/281 |
| 5,927,277 A | * | 7/1999 | Baudino et al. | 600/386 |
| 2009/0088826 A1 | * | 4/2009 | Bedenbaugh | 607/116 |

* cited by examiner

*Primary Examiner* — Christopher Beccia
(74) *Attorney, Agent, or Firm* — Porzio, Bromberg & Newman, P.C.

(57) ABSTRACT

A plate used in neurological cranial surgeries having a set of grooves and holes providing it with multiple functions: radial groove with semicircular end sufficient to receive a drain or catheter; central round hole, sufficient to receive a second drain or catheter; three curved oblong holes around the central circular hole and the borders with ends adjacent to the semicircular end of the radial groove. The plate provides a useful area, on which the following are disposed: the semicircular end of the radial groove, the central round hole and the curved oblong.

9 Claims, 6 Drawing Sheets

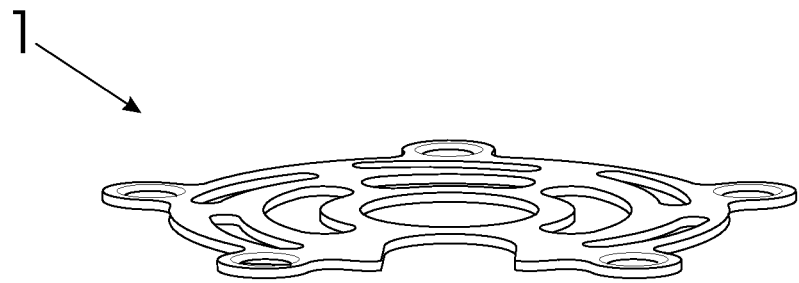
FIG. 4
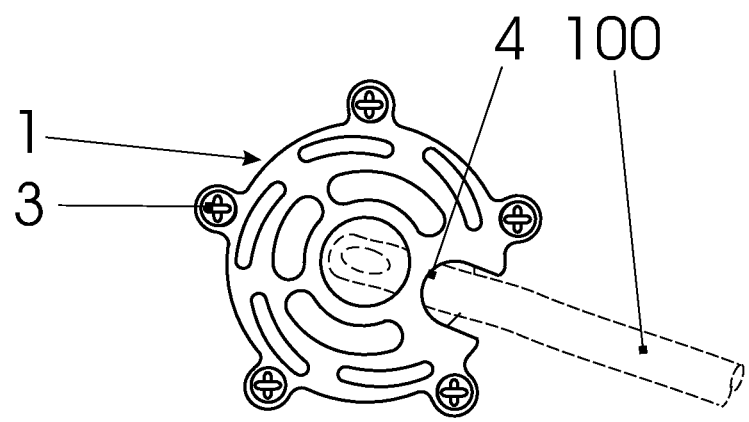
FIG. 5 "A"

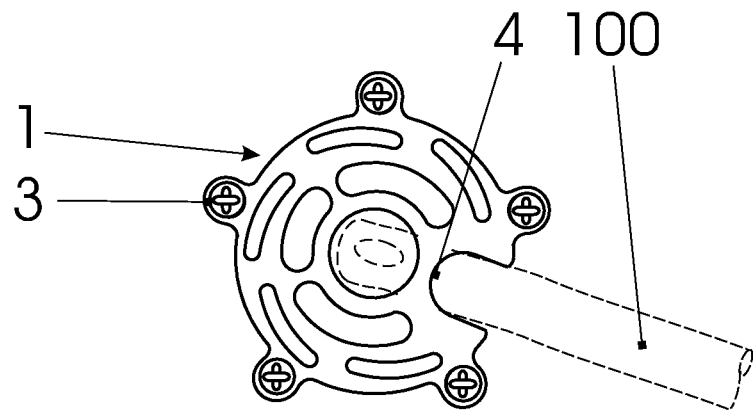
FIG. 5 "B"
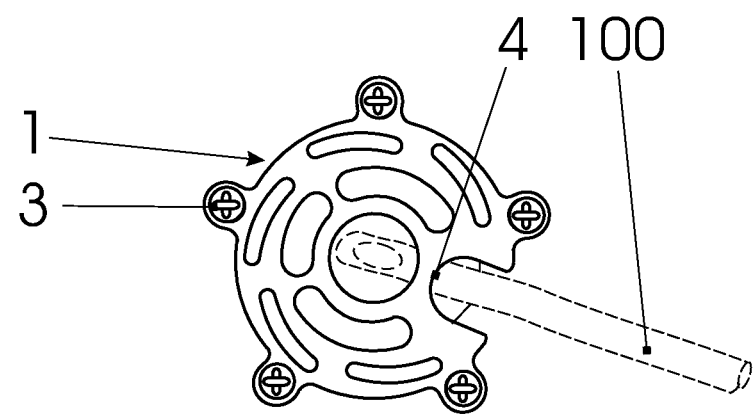
FIG. 5 "C"

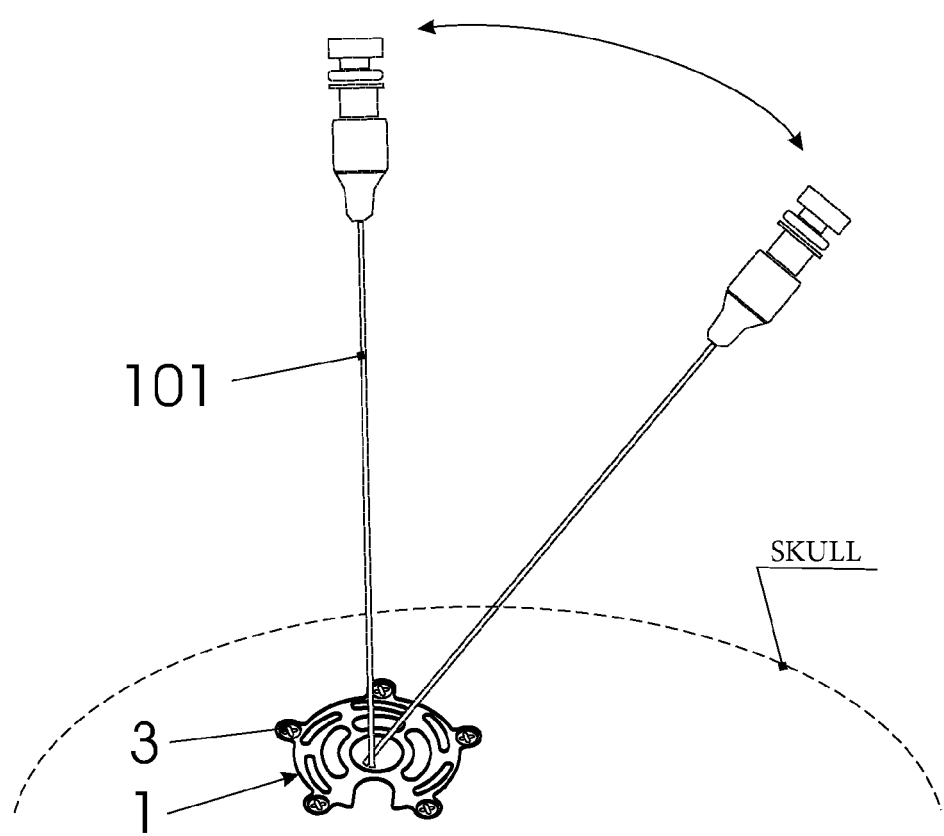
FIG. 7"A"

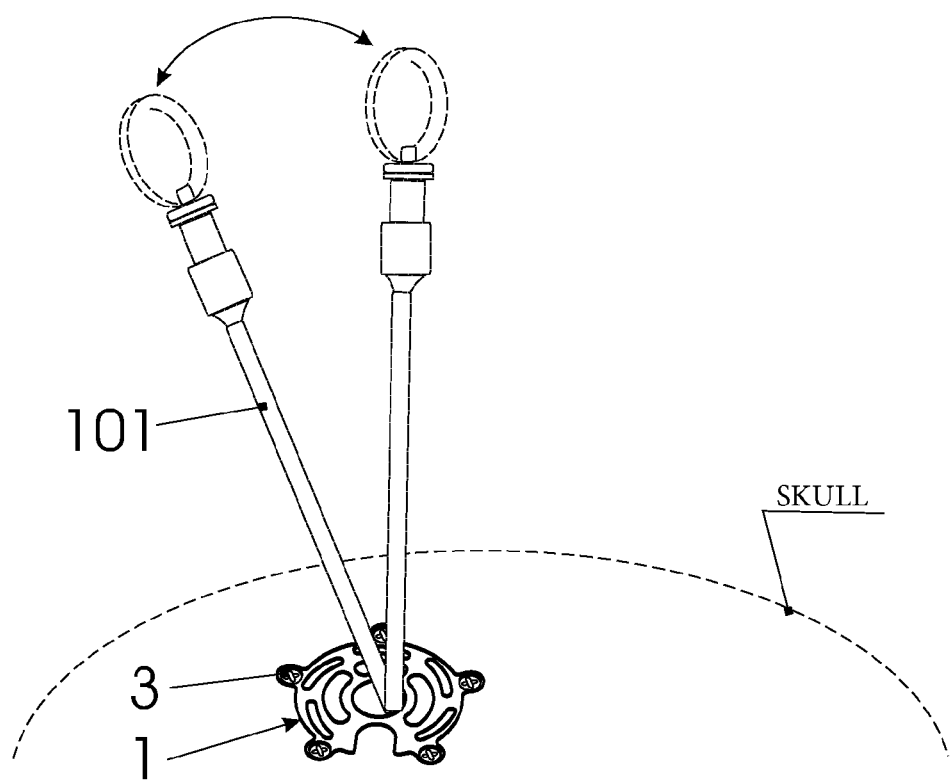
FIG. 7"B"

MULTIFUNCTIONAL PLATE FOR NEUROLOGICAL CRANIAL SURGERIES

CROSS-REFERENCE TO RELATED APPLICATION

This application claims priority on PI 1105137-0 filed in Brazil on Dec. 16, 2011, hereby incorporated in its entirety by reference into this application.

INTRODUCTION

This descriptive report refers to a patent for an invention related to a plate used in neurological cranial surgeries, pertaining to the field of products used in medicine and which has been developed to provide a number of functions for application.

STATUS OF TECHNIQUE

In practice, most of the neurological cranial surgeries star by performing a skull perforation, the so called Skull Terpanation procedure. The hold resulting from such procedures is called Terpanation Hole.

Sometimes, in minor surgeries, the only required surgical access to the brain is performed by means of a single Skull Trepanation. In other instances, requiring a higher brain exposure, when the removal/opening of a higher skull portion (Craniotomy) is required, such procedure is performed by means of one or several Trepanation, through which instruments are passed, such as a wired saw (Gigli saw) or an automated saw, which turns around its own shaft, as a metal grip, driven by electricity or compressed gas (Craniotome).

After the procedure, the Trepanation Holes can and shall be occluded in order to protect the underlying brain tissue and due to esthetic and hygienic reasons, so that no depressions can be visible (where dirty is likely to accumulate) and palpable in the patient's skull. Such occlusion is performed in the skull closure phase, after the completion of the main phase and the closure of the brain protection membrane, the Dura-Mater.

The Skull Trepanation Holes can be occluded by different means, among which is the use of Titanium Skull Occlusion Plates. Such plates have an essentially round or polygonal (star) shape, are provided, throughout their area, with a number of holes for the spontaneous release of residual fluids and, also, to help with the scalp attachment process to the plate itself by means of the formed healing tissue which get into such small holes. There are also peripheral holes which receive micro screws made of Titanium intended to attach such plates on the skull in order to occlude the Trepanation Hole and also, in cases on which Craniotomies were performed, such plates help to stabilize/attach the skull bone flap in the skull borders. This type of plate can be visualized, for example, in patent U.S. Pat. No. 5,201,737.

On the other hand, Titanium plates similar to those described above are also know, however, they are intended to receive drains or catheters used in specific medical procedures. The plates have a radial groove allowing the passage of a drain and/or catheter. These plates are only intended to receive drains and/or catheters and this is why they have a radial groove extended through great part of the diametric extension, around ¾ of the extension, turning it excessively flexible. Thus, due to the great flexibility, such plates are not appropriate to help in stabilizing/attaching the bone flap.

Therefore, when a medical procedure requires the Trepanation Hole to be occluded and/or stabilization/attachment of a bone flat and requires the use of drains and/or catheters (on a transitory or permanent basis) the use of both types of plates is required.

An inconvenient verified with the above described plates consists in the fact that Nelaton drains, particularly those used in South America and presenting higher diameters, when removed, get hooked up in the plate, being likely to be ruptured inside the skull leading to a re-surgery in order to remove it.

OBJECTIVES OF THE INVENTION

Therefore, this invention is intended to provide a more versatile plate for cranial surgeries, allowing the passage of drains or catheters, providing transcutaneous access to surgical instruments, such as puncture of biopsy needles and which can further help in the stabilization/attachment of the bone flap in Craniotomy procedures.

Another objective is to provide a low profile plate, with optimal cosmetic effect and, even though, with increased resistance, easy to be implanted, providing, on a safe way, the passage or the removal of drains/catheters. If we consider the wide central hole, in addition to the radial groove, it can allow the exit of a second drain or catheter at the same time, in situation on which this becomes necessary.

Another objective is to provide a plate meeting the objectives above and manufactured with biocompatible materials and already established in medicine, so as to mostly prevent the side effects to the human being.

Another objective is to provide a plate which allows a better evaluation of the blood supply of the brain through a wide central hole which decreases the resistance to Ultrasound waves (Transcranial Doppler) in specific medical situations.

SUMMARY DESCRIPTION OF THE INVENTION

In the view of the limits mentioned above related to the conventional plates and in order to overcome them and in order to meet the related objectives, the multifunctional plate was developed for neurological cranial surgeries, object of this patent, which comprises a round contour Titanium plate body provided with peripheral holes intended to receive Titanium micro screws in order to attach it to the skull. This invention has a series of advantages providing multiple functions to the plate: a radial groove with semicircular end being wide enough for the passage of a drain or catheter whose radial extension does not exceed around ¼ of the plate's diameter; a round central hole being sufficiently sized for the passage of a second drain or catheter; three curved oblong holes, located around part of the central round hole, being that, such external curved oblong holes present ends adjacent to the opposite side of the radial groove, the said oblong holes, the central round hole and the semicircular end of the radial grove define a central useful area whose configurations are arranged in such a way to provide transcutaneous access to the intracranial cavity with surgical instruments such as puncture, biopsy needle or other instruments at different positions; the said radial groove, central round hole and curve oblong holes have selected sizes so as to meet their intended functions and to define, among them and the plate border, material strips sized to, along with the radial groove extension lower than ¼ of the plate diameter, provide that the plate is more rigid, not very flexible, so that it can also be used a support plate for the stabilization/attachment of the bone flap in Craniotomy procedures; such useful area, containing the semicircular end of the radial groove, the central round hole and the curved oblong holes, further allows an improved passage/reading of the Ultrasound waves (Transcranial Doppler) compared with the other conventional plates which are more compact/closed, when used to cover the trepanation hole under which there is practically no bone resistance.

Therefore, the plate with the characteristics above, is multifunctional, versatile, once it covers a number of functions required functions in neurological cranial surgeries, such as: exit/passage of one or two drains and/or catheters; transcutaneous access to the intracranial cavity through puncture or biopsy needles or other instruments; support for the stabilization/attachment of the bone flap in Craniotomy procedures and the advantage of favoring/improving the reading of the Transcranial Doppler Ultrasound waves.

The fact that the radial groove does not exceed 25% of the plate's diameter, different from what is noted in relation to the other existing plates, associated to an increased provision of material strips between the grooves and holes, causes this plate to be more resistant and stable being, therefore, also used as a support for the attachment of the bone flap to the skull in cases of Craniotomies, in the most different positions of plate attachment.

Further, this plate's radial groove and central round hole have configurations which prevent the drains (particularly Nelaton drains, of increased diameter) from being hooked up in the plat itself providing, thus, the safe removal of the same and, in the same way, the safe removal of catheters, providing the patient safety and increased tranquility to the surgeon.

This plate also meets other requirements, such as: low profile; appropriate resistance; easy application; optimal cosmetic effect.

LIST OF DRAWINGS

The attached drawings refer to the multifunctional plate for neurological cranial surgeries, object matter of this patent, on which:

FIG. 4 shows the plate in perspective view;

Figure 6:
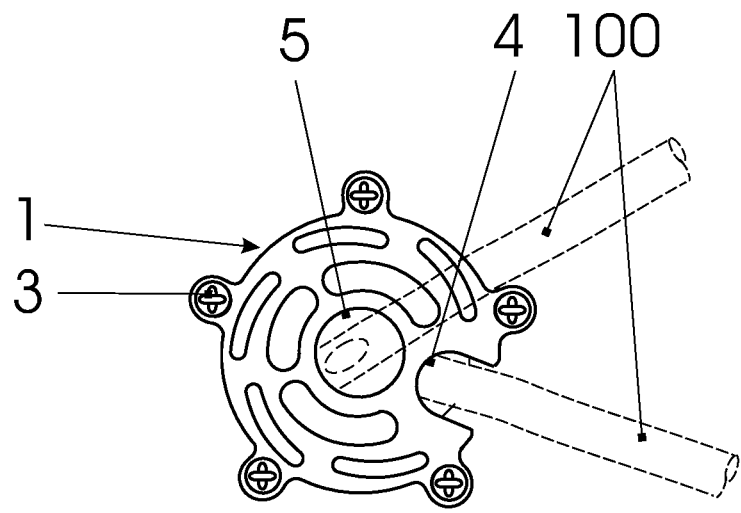
Figure 8:
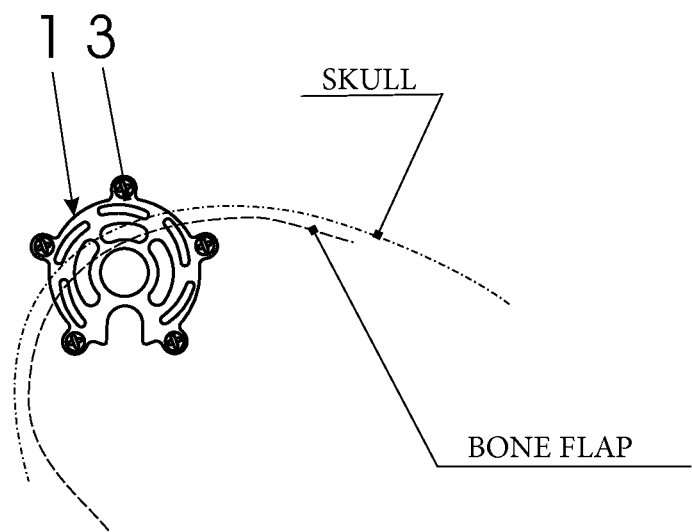

FIGS. 5 "A"; 5 "B" and 5 "C" show the plate receiving, in its radial groove, drains or catheters of different diameters;

FIG. 6 show the applied plate and the exit of two drains on a simultaneous way, one in the radial groove and another one in the central round hole;

FIGS. 7 "A" and 7 "B" show the plate applied and used along with surgical instruments (puncture or biopsy needle) in procedures of transcutaneous access to the intracranial cavity;

FIG. 8 shows the plate used to help with the stabilization/attachment of bone flat in a Craniotomy procedure.

DETAILED DESCRIPTION BASED ON THE DRAWINGS

As shown by the figures listed above, the multifunctional plate for neurological cranial surgeries, object matter of this patent, comprises (FIG. 1) a Titanium round plate body 1, with small peripheral radial round projections provided with holes 2 intended to receive Titanium micro screws 3 for attachment to skull.

In this invention, the plate has a set of grooves/holes providing the same with multiple functions (FIG. 1): radial groove with an end which is semicircular 4 enough to receive a drain or catheter; central round hole 5, sufficient to receive a second drain or catheter; three curved oblong holes 6 around the central round hole 5 and the external curved oblong holes 6 with ends adjacent to the semicircular end of the radial groove 4.

Figure 2:
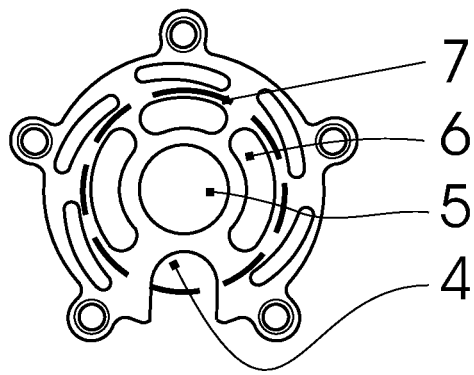
FIG. 2 shows the same previous figure, but indicating the plate's useful area.

The referred plate provides a useful area 7 (FIG. 2), on which the following are disposed: the semicircular end of the radial groove 4, the central round hole 5 and the curved oblong holes 6 with configuration and are arranged in such a way to provide transcutaneous access to the intracranial cavity through surgical instruments such as puncture of biopsy needle or others; the central round hole 5 also allows a better reading of Ultrasound waves for being in contact with a place of the skull on which there is practically no bone resistance.

Figure 3:
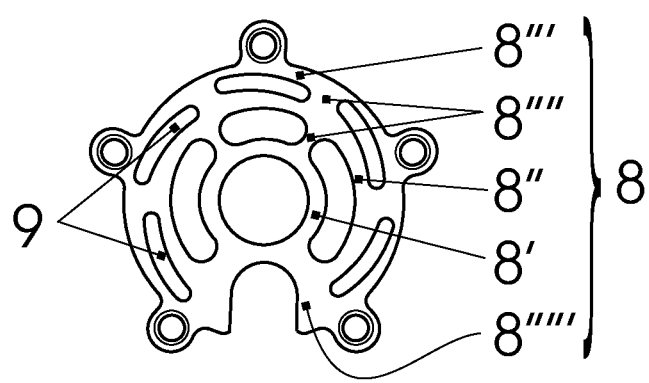
FIG. 3 shows the same previous figures, but this one identifies the material strips defined between the plate's grooves and holes providing resistance to it with numeric references.

The radial groove 4, the central round hole 5 and the curved oblong holes 6 (FIGS. 1, 3) have sizes selected to accomplish its function and to define among them and between them and the border of the plate material strips 8 sized in such a way to help in providing resistance to the plate, so that it can be also used as a plate intended to stabilize/attach the skull bone flap in Craniotomy operations.

In details, the radial groove 4 is 4.5 mm wide and length with around ¼ of the plate diameter sufficient to allow the passage of drains or catheters 100 which need to be left inside the skull, whether on a permanent or transitory basis (FIGS. 5"A", 5"B" and 5"C";). The radial groove 4 extends from the plate's border, where it is open, to the semicircular end being, therefore, non-cutting and adjacent to the central round hole 5.

Figure 1:
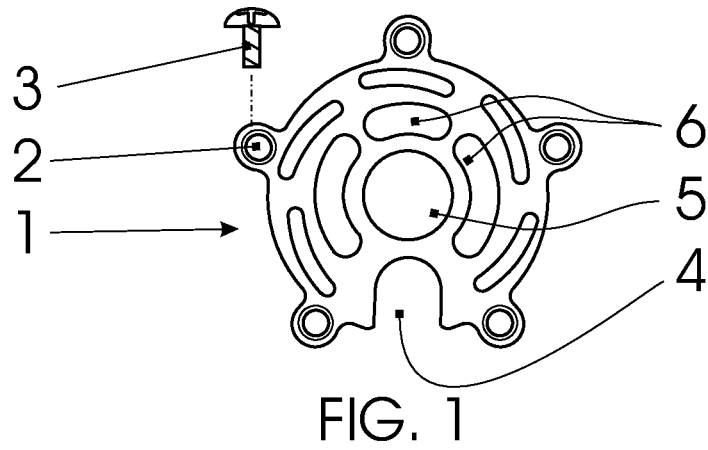
FIG. 1 shows the plate from the front view.

The central round hole 5 is 6.0 mm in diameter and works as a second hole for the passage of a second drain/catheter 100 (if required) having, therefore, round, i.e., non-cutting borders (FIGS. 1, 6).

Thus, the plate can be used for the passage/exit of a drain or catheter as shown in FIGS. 5"A", 5"B", 5"C" or for the simultaneous passage/exit of two drains or two catheter or a drain and a catheter, as shown in FIG. 6.

The central round hole 5, the three curved oblong holes 6 and the semicircular end of the radial groove 4 complete the useful area 7 and are configured and arranged in such a way to allow the surgeon, in case of specific emergencies, a transcutaneous and immediate access to the intracranial cavity through puncture or biopsy needle 101 (FIGS. 7"A", 7"B"), being likely to reach on a cross or angled way relapsed pathologies requiring re-treatment/drainage such as, for example, liquefied hematomas, abscesses and underlying brain cysts. In addition, the central hole 5 allows for a better reading of the Ultrasound waves (Transcranial Doppler) when this exam is required, because, corresponding with the central round hole 5, there is practically no bone resistance in the skull.

The fact that the radial groove 4 does not exceed 25% of the total diameter of the plate, different from other plates existing in the market which exceed such value, associated with the fact that the material strips 8, located between the radial groove 4 and the central round hole 5 and the curved oblong holes 6 and between them and the plate border are foreseen, it makes this plate more resistant and more stable being, therefore, used as a support for the attachment of the bone flap to the Skull, in cases of Craniotomies (FIG. 8) in the several positions at which the plate can be attached.

The material strips 8 comprise (FIG. 3): ring-like stripe 8' around the central round hole 5 and between this and the semicircular end of the radial groove 4 and the curved oblong holes 6; first peripheral ring-like strip 8" located between the curved oblong holes 6 and narrow oblong peripheral holes 9 and second peripheral ring-like stripe 8''' located between the latest ones and the border of the plate; the referred material strips 8 further comprise: radial strips 8'''' located between the curved oblong holes 6; between the peripheral oblong holes 9 and lateral to the radial groove 4. These strips, along with the decreased length of the radial groove, 25% of the diameter, provide the plate with rigidity which allows to use it as an auxiliary means for the attachment of the bone flap.

Within the basic construction described above, the plate, object matter of this patent, can present changes related to materials, sizes, construction and/or functional and/or ornamental configuration details, without departing from the scope of the requested protection.

The invention claimed is:

1. A plate with multiple functions for neurological cranial surgeries comprising a circular Titanium plate body provided with peripheral holes which are receptors of Titanium micro screws for fixation in the cranium in order to attach the plate body to the skull, said plate having a set of grooves and holes that provide passages which assign multiple functions to the plate, a radial slot with a semicircular end sufficient to receive a first drain or catheter;

a central circular hole, sufficient to receive a second drain or catheter;

three curved oblong holes arranged around the central circular hole;

said plate provides one per area of use in which the semicircular end of the radial slot, the central circular hole and the curved oblong holes; the said radial slot, the central circular hole and the curved oblong holes are arranged and have configurations and are arranged to provide transcutaneous access of the intracranial cavity via surgical instruments;

the radial slot, the central circular hole and the curved oblong holes have dimensions selected to perform its functions and to define between themselves and between themselves and the edge of the plate strips of material sized to help to give rigidity to the plate;

wherein the area provided by the central circular hole, the three curved oblong holes and the end semicircular radial slot defines the area of use for transcutaneous and immediate access to intracranial cavity through a puncture or biopsy needle and, said radial slot, the central circular hole and the curved oblong holes having settings and are arranged to enable the surgical instruments to achieve, in a cross shape or angled shape, recurrence pathologies, which need to be treated/drained again in recent or late postoperative; the said area of use acts to allow better reading of Ultrasound waves by locating/ being in correspondence of the site in the skull in which there is practically no bone strength.

2. The plate with multiple functions for neurological cranial surgeries according to claim 1, wherein the radial slot has a width and the semicircular end of the radial slot has enough width and length to allow passage of drains or catheters;

said radial slot extends from the edge of the plate, which is open, to the semicircular edge, so non-cutting, adjacent to the central circular hole.

3. The plate with multiple functions for neurological cranial surgeries according to claim 1, wherein the radial slot has a width of 4.50 mm and a length without exceeding ¼ of the diameter of the plate.

4. The plate with multiple functions for neurological cranial surgeries according to claim 1, wherein the central circular hole has a diameter sufficient to allow the passage of a second drain or catheter, said hole being circular, and having rounded non-cutting edge.

5. The plate with multiple functions for neurological cranial surgeries according to claim 1, wherein the central circular hole with has a diameter of 6.00 mm.

6. The plate with multiple functions for neurological cranial surgeries according to claim 1, wherein it could serve for stabilization placement/passage of a drain or catheter applied in the radial slot or the central circular hole or serve for simultaneous stabilization placement/passage of two drains or two catheters or a drain and catheter applied in the radial slot and a central circular hole.

7. The plate with multiple functions for neurological cranial surgeries according to claim 1, wherein the radial slot has a selected length not to exceed 25% of the diameter of the plate.

8. The plate with multiple functions for neurological cranial surgeries according to claim 1, wherein material strips comprise an annular band disposed around the central circular hole and between this and the semicircular end of the radial slot and the curved oblong holes;

a first peripheral annular band located between the curved oblong holes and narrow oblong peripheral holes and a second peripheral annular band located between the narrow oblong peripheral holes and the edge of the plate;

radial strips located between the curved oblong holes; between the peripheral oblong holes and lateral to the radial slot.

9. The plate for neurological cranial surgeries according to claim 1, wherein the length of the radial slot, is less than 25% of the diameter of the plate, associated with the material strips situated between the radial slot, the central circular hole and the curved oblong holes and between the latter and the edge of the plate are selected to give it the necessary rigidity to act as an auxiliary plate to fix the bone flap in cases of craniotomy.

* * * * *